(12) United States Patent
Endermann et al.

(10) Patent No.: US 8,034,817 B2
(45) Date of Patent: Oct. 11, 2011

(54) TREATMENT OF BACTERIAL DISEASES OF THE RESPIRATORY ORGANS

(75) Inventors: Rainer Endermann, Wuppertal (DE); Harald Labischinski, Wuppertal (DE); Christoph Ladel, Ivrea (IT); Uwe Petersen, Leverkusen (DE); Ben Newton, Amersham (GB)

(73) Assignee: Bayer Pharma Aktiengesellschaft, Berlin (DE)

( * ) Notice: Subject to any disclaimer, the term of this patent is extended or adjusted under 35 U.S.C. 154(b) by 1201 days.

(21) Appl. No.: 10/775,888

(22) Filed: Feb. 10, 2004

(65) Prior Publication Data
US 2004/0254194 A1    Dec. 16, 2004

(30) Foreign Application Priority Data

Feb. 10, 2003  (DE) .................................. 103 05 318
Feb. 10, 2003  (DE) .................................. 103 05 319

(51) Int. Cl.
*A61K 31/497* (2006.01)
*A61K 9/14* (2006.01)
*A61K 9/00* (2006.01)
*A61K 9/12* (2006.01)

(52) U.S. Cl. ................... 514/253.08; 424/489; 424/400; 424/43; 424/46

(58) Field of Classification Search .............. 514/253.08
See application file for complete search history.

(56) References Cited

U.S. PATENT DOCUMENTS

| 4,670,444 | A |   | 6/1987 | Grohe et al. .................. 514/300 |
| 4,990,517 | A |   | 2/1991 | Petersen et al. ............... 514/300 |
| 5,607,942 | A |   | 3/1997 | Petersen et al. ............... 546/200 |
| 5,808,076 | A | * | 9/1998 | Vetter et al. ................... 546/156 |
| 2004/0009126 | A1 | * | 1/2004 | Pilkiewicz et al. ............. 424/46 |
| 2004/0024018 | A1 | * | 2/2004 | Kanikanti et al. ............. 514/312 |

FOREIGN PATENT DOCUMENTS

| EP | 0049355 A1 | 8/1981 |
| EP | 0049355 B1 | 8/1981 |
| EP | 0350733 A2 | 6/1989 |
| EP | 0350733 B1 | 6/1989 |
| WO | 0145679 A2 | 12/2000 |
| WO | WO 0200219 A1 * | 1/2002 |

OTHER PUBLICATIONS

Mayer et al. Clinical presentation of inhalational anthrax following bioterrorism exposure, JAMA, Nov. 21, 2001, vol. 286, No. 20, pp. 2549-2553.*
Li et al. Ciprofloxacin-loaded bovine serum albumin microspheres preparation and drug-release in vitro, J. Microencapsulation, 2001, vol. 18, No. 6, p. 825-829.*
IUPAC "betaine" Jan. 5, 2010.*
STN registration file: Ciprofloxacin betaine, 2011.*
Bayer Healthcare Pharmaceuticals, Inc., CIPRO XR Package Insert, Oct. 2008.
Caco et al., Solubiiity of Antibiotics in Different Solvents, Part II. Non-Hydrochloride Forms of Tetracycline and Ciprofloxacin, Ind. Eng. Chem. Res. 2008, 47, 8083-8089.

* cited by examiner

*Primary Examiner* — Shengjun Wang

(57) ABSTRACT

The invention relates to inhalable quinolonecarboxylic acid derivative compositions for local control of diseases of the respiratory organs, in particular of lung diseases.

3 Claims, No Drawings

TREATMENT OF BACTERIAL DISEASES OF THE RESPIRATORY ORGANS

RELATED APPLICATIONS/PATENTS AND INCORPORATION BY REFERENCE

This application claims priority under to German Patent Application No. 103 05 318.2, filed Feb. 10, 2003, and to German Patent Application No. 103 05 319.0, filed Feb. 10, 2003, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present invention relates to the use of dosage forms which contain quinolonecarboxylic acid derivatives and enable local treatment of diseases of the respiratory organs, in particular lung diseases caused by bacteria.

Despite enormous progress in the area of controlling bacterial infectious diseases through the introduction of various classes of antibiotics in the last 70 years, severe lung infections still represent an important problem, especially in relation to pathological states such as cystic fibrosis, bronchiectasis and increasingly also chronic obstructive pulmonary diseases (COPD), which are associated with infections which can be treated only with difficulty or not at all. Active ingredients from the class of fluoroquinolones, especially also moxifloxacin and ciprofloxacin, are frequently employed for the treatment of such diseases because of their relevant range of antibacterial effects and their bactericidal action.

Moxifloxacin hydrochloride (I)

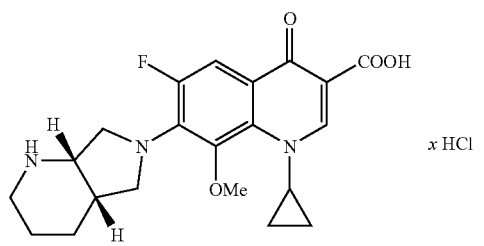

is an antibacterial active ingredient from the class of quinolonecarboxylic acid derivatives for the treatment and prevention of otitis, pharyngitis, pneumonia, peritonitis, pyelonephritis, cystitis, endocarditis, systemic infections, acute and chronic bronchitis, septic infections, diseases of the upper airways, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmons, wound infections, infected burs, burns, infections in the oral region, infections after dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid, meningitis, infections of the nervous system, salpingitis, endometritis, genital infections, pelveoperitonitis and eye infections (EP 350 733 B1, U.S. Pat. Nos. 4,990,517, 5,607,942 and WO 01/45679). The principal indications for moxifloxacin are diseases of the respiratory tract, especially of the lungs.

Dosage forms for moxifloxacin mentioned in EP-B 350 733 are tablets, coated tablets, capsules, pills, granules, suppositories, solutions, suspensions and emulsions, pastes, ointments, gels, creams, lotions, dusting powders and sprays. To our knowledge, only tablets and (for intravenous administration) solutions are on the market.

In practice, moxifloxacin has to date been used exclusively systemically for all diseases for the control of which it is suitable (including those of the lungs). The reason for this is the high oral bioavailability and the good distribution of the active ingredient. Although the increase in the active ingredient concentration in the serum and lungs of rats after local (intratracheal) administration of moxifloxacin hydrochloride is greater than with systemic (oral) administration of the same amount of moxifloxacin hydrochloride, its concentration also falls relatively rapidly (within about an hour) to the level of the concentration reached orally, so that intratracheal local administration achieves no advantages compared with oral administration in experiments on rats too.

Ciprofloxacin hydrochloride and enrofloxacin hydrochloride (II) are antibacterial quinolonecarboxylic acid derivatives which have been known for about 20 years (EP-B 49 355, U.S. Pat. No. 4,670,444) and which can be employed extremely successfully both for the prophylaxis and for the treatment of systemic and local bacterial infections, especially of the urinary tract. Ciprofloxacin is also effective inter alia against anthrax pathogens.

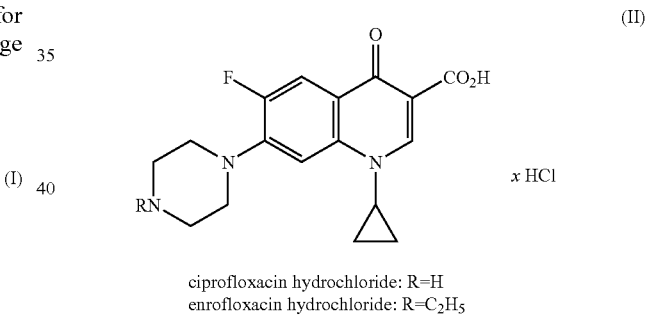

ciprofloxacin hydrochloride: R=H
enrofloxacin hydrochloride: R=$C_2H_5$

The dosage forms of ciprofloxacin/enrofloxacin mentioned in EP-B 49 355 are tablets, coated tablets, capsules, pills, granules, suppositories, solutions, suspensions and emulsions, pastes, ointments, gels, creams, lotions, dusting powders and sprays. Ciprofloxacin tablets, suspensions, eye and ear drops and solutions suitable for intravenous infusion are currently on the market.

It has been found, surprisingly, that control of diseases of the respiratory organs, especially lung diseases caused by bacteria, is extremely successful when ciprofloxacin or enrofloxacin is administered locally as solid betaine and/or as solid slightly soluble betaine salt. The active ingredient concentration in the lungs can be kept for a lengthy period at a level desirable from the medical viewpoint for optimal treatment. Besides the higher and long-lasting active ingredient level at the site of the infection, it is possible to achieve simultaneously a comparatively low systemic concentration of the active ingredient, so that side effects of the medication and the disquieting development of resistance through systemic selection pressure are at least drastically reduced or even entirely prevented in this way.

The invention therefore relates to a method for controlling diseases of the respiratory organs, especially lung diseases caused by bacteria, in humans and animals by local administration of an antibacterially effective amount of solid betaine of the formula (III)

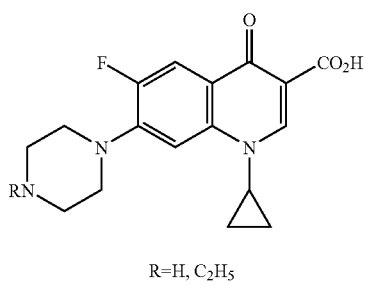

(III)

R=H, C$_2$H$_5$ and/or of its solid slightly soluble salt and to the use of these compounds for producing medicaments for the local control of diseases of the respiratory organs, especially lung diseases caused by bacteria, in humans and animals, where the compounds are administered in solid form.

"Slightly soluble salts" for the purposes of the invention have a solubility in water of less than 0.1, preferably less than 0.01,% by weight based on water at 25° C. and a pH of 7. Such slightly soluble salts include C$_{16}$-C$_{18}$ fatty acid salts of the betaine (III) and salts of the betaine (III) with acids such as, for example, the embonates or else salts of the betaine (III) with bases such as N,N'-dibenzylethylenediamine.

The invention relates in a preferred embodiment to a method for controlling diseases of the respiratory organs, especially lung diseases caused by bacteria, in humans and animals by local administration of an antibacterially effective amount of solid betaine of the formula (III) and/or its embonate and to the use of these compounds for producing medicaments for the local control of diseases of the respiratory organs, especially lung diseases caused by bacteria, in humans and animals, where the compounds are administered in solid form.

In a particular embodiment of the invention, the diseases of the respiratory organs comprise diseases, caused by bacteria, of the airways or of the lungs, especially lung diseases caused by bacteria.

The embonates (also called pamoates) are salts of embonic acid, corresponding to formula (IV a) and/or (IV b):

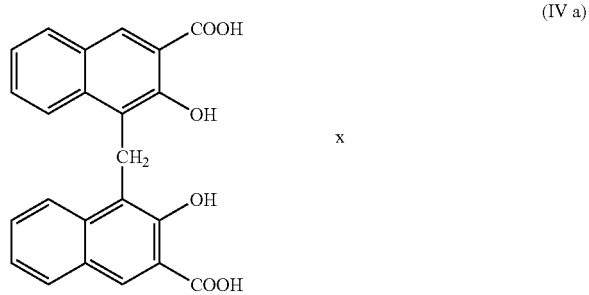

(IV a)

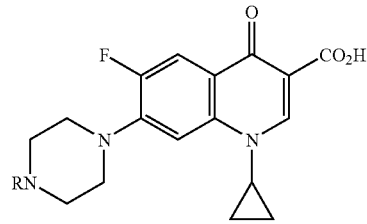

R = H, C$_2$H$_5$

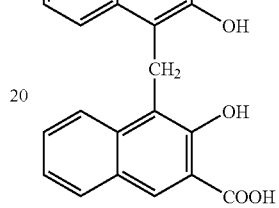

(IV b)

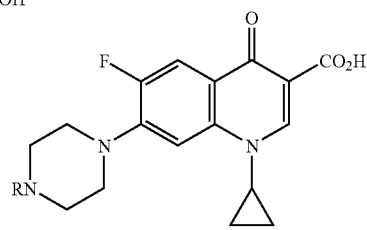

The term "embonate" refers for the purposes of the invention to the embonate, the hemiembonate and to mixtures thereof.

The term "respiratory organs" (or respiratory system) refers for the purposes of the invention to the nose, oral cavity and pharynx, and the larynx, trachea and lungs, including the airways and the paranasal sinuses and frontal sinus, where "airways" (or respiratory tract) mean the nasal cavity, oral cavity, pharynx, larynx, trachea and bronchi.

"Local administration" or "local control" in connection with diseases of the respiratory organs, especially lung diseases, means for the purposes of the invention—in contrast to oral administration of dosage forms intended for absorption via the gastrointestinal tract, and in contrast to intravenous administration—administration of the active ingredient by inhalation in inhalable dosage form. The preparation in powder form or powder-containing suspensions to be used according to the invention are preparations which are aerosolized and then inhaled.

The term "inhalation" or "administration by inhalation" refers in this connection to the introduction into the respiratory organs, especially into and/or via the airways, preferably into and/or via the nasal cavity and oral cavity.

The term "intratracheal" or "intratracheal administration" refers for the purposes of the invention to introduction into the trachea not by inhalation, in particular for pulmonary disease control in experimental animals such as rats as a model of administration by inhalation.

The invention further relates to devices which contain preparations containing betaine (III) and/or its solid slightly soluble salt, in particular its embonate, and which are suitable for the administration by inhalation thereof in solid form, i.e. aerosolizers which are able to administer preparations containing betaine (III) and/or its solid slightly soluble salt, in particular its embonate, by inhalation in solid form (powder inhalers), or aersolizers which are able to administer suspensions containing betaine (III) and/or its solid slightly soluble salt, in particular its embonate, in solid form by inhalation (suspension sprays).

Solid preparations for dry powder inhalation or suspension inhalation will generally contain an amount of active ingredient (i.e. betaine (III) and/or its solid slightly soluble salt, in particular its embonate) which is as high as possible. The amount of active ingredient therein is usually at least 60, preferably at least 70, in particular at least 80 and most preferably at least 90,% by weight based on the preparation ready for use. However, the amount of active ingredient therein may also be less than 60% by weight based on the preparation ready for use and is then preferably at least 30, in particular at least 40,% by weight based on the preparation ready for use. Where no adjuvants are necessary, especially in the case of solid preparations for suspension inhalation, they may also consist of active ingredient alone. However, for practical reasons, the preparations according to the invention are often medicaments which, besides the active ingredient, contain one or more pharmacologically acceptable excipients. A review of various suitable preparations and corresponding administration aids is to be found for example in R. Stangl, "An Overview of Innovative Inhalation Devices", European Pharmaceutical Review, pages 50-55, (2002) and the literature cited therein. Pharmacologically acceptable excipients include, inter alia, binders (e.g. maize starch, gelatin), stabilizers (e.g. antioxidants such as ascorbic acid), carriers (e.g. microcrystalline cellulose, lactose, sucrose, calcium phosphate, maize starch), lubricants (e.g. talc, stearic acid, magnesium stearate, calcium stearate or zinc stearate), flavourings and/or fragrances. The production of suitable preparations by selecting suitable excipients in terms of nature and quantity is straightforward.

The preparations according to the invention can be produced—as is usual in the production of inhalable free-flowing medicaments in powder form, by micronizing the active ingredient or by spray drying appropriate solutions or suspensions.

The solid preparations generally have a particle diameter, determined as volume median (with the aid of a laser diffraction apparatus), of from 0.2 to 15 µm, preferably from 1 to 5 µm. The diameter determined as volume median is the value below and above which 50% of the volume of the particles lie.

In a preferred embodiment, the solid preparations have particle diameters, determined as 50% of volume median, of from 2 to 5 µm and particle diameters, determined as 90% volume proportion, of from 6 to 10 µm. In a further preferred embodiment, the solid preparations contain active ingredient, in particular ciprofloxacin betaine, with a particle diameter, determined as 50% volume median, of from 2 to 5 µm and particle diameters, determined as 90% volume proportion, of from 6 to 10 µm. The diameter determined as 50% or 90% volume proportion (with the aid of a laser diffraction apparatus) is the value below which respectively 50% and 90% of the volume of the particles lie. Thus, for example, in a solid preparation with a particle diameter, determined as 50% volume median, of 2 µm and a particle diameter, determined as 90% volume proportion, of 6 µm. (50%<2 µm; 90%<6 µm) the particle diameter of 50% of the volume of the particles is below 2 µm and of 90% of the volume of the particles is below 6 µm.

It has generally proved advantageous in administration by inhalation to administer amounts of about 0.1 to 20, preferably about 0.5 to 7.5, mg/kg of bodyweight to achieve effective results.

It may nevertheless be necessary to depart from the stated amounts, specifically as a function of the bodyweight, individual behaviour towards the active ingredient, nature of the preparation and time or interval over which administration takes place. Thus, it may suffice in some cases to make do with less than the aforementioned minimum amount, whereas in other cases the said upper limit must be exceeded. Where larger amounts are administered, it may be advisable to divide them into a plurality of single doses over the day.

EXAMPLES

Preparation of Ciprofloxacin Embonate a) Ciprofloxacin Embonate (IV a; R=H)

33.1 g (0.1 mol) of ciprofloxacin betaine and 38.8 g (0.1 mol) of embonic acid are heated in 500 ml of glycol monomethyl ether under reflux for 1 hour. After cooling, the precipitate is filtered off with suction, thoroughly washed with ethanol and dried at 120° C. under high vacuum.

b) Ciprofloxacin-Hemiembonate (IV b; R=H)

66.2 g (0.2 mol) of ciprofloxacin betaine and 38.8 g (0.1 mol) of embonic acid are heated in 500 ml of glycol monomethyl ether under reflux for 1 hour. After cooling, the precipitate is filtered off with suction, thoroughly washed with ethanol and dried at 120° C. under high vacuum.

Determination of the Active Ingredient Concentration in the Lungs of Rats

Female Wistar rats (80 to 100 g) were treated with

A1—7.5 mg/kg ciprofloxacin betaine (laboratory product) intratracheally as suspension;

A2—7.5 mg/kg ciprofloxacin betaine (micronized: 50%<3 µm; 90%<7 µm) intratracheally as suspension;

B—7.5 mg/kg ciprofloxacin hydrochloride intratracheally as solution;

C—7.5 mg/kg ciprofloxacin-hydrochloride intravenously as solution.

Three animals from each of the dose groups were sacrificed after 0.25, 0.5, 1, 3 and 5 hours, and the lungs were removed. The lungs were homogenized using a Potter from Braun. The active ingredient content in the lung homogenates was determined by bioassay.

Pharmacokinetic Parameters for the Lungs

| Dose group | AUC [mg*h/l] | $C_{max}$ [mg/l] | $t_{1/2}$ [h] |
|---|---|---|---|
| A1 | 124 | 49.1 | 1.96 |
| A2 | 304 | 76 | 13.47 |
| B | 3.20 | 6.65 | 0.847 |
| C | 0.497 | 0.610 | 0.758 |

Lung Concentrations in µg/ml; Averages for 3 Animals

| Dose group | 0.25 h | 0.5 h | 1 h | 3 h | 5 h |
|---|---|---|---|---|---|
| A1 | 49.1 | 44.3 | 40.1 | 12.6 | 7.21 |
| A2 | 76 | 76 | 76 | 54 | 54 |
| B | 6.65 | 1.67 | 0.63 | 0.10 | 0 |
| C | 0.61 | 0.35 | 0.14 | 0 | 0 |

AUC, $C_{max}$ and $t_{1/2}$ are important pharmacokinetic parameters for describing pharmacokinetic/pharmacodynamic interactions; cf., for example, W. A. Craig, "Pharmacokinetic/pharmacodynamic parameters: rationale for antibacterial dosing of mice and men", Clin. Infect. Dis. 26, 1-12 (1998).

Intratracheal administration of ciprofloxacin-betaine (laboratory product) reveals, compared with intratracheal administration of ciprofloxacin-hydrochloride, a 40 times larger AUC and an 8 times higher $C_{max}$. This kinetic advantage becomes even clearer on comparison with intravenous administration of ciprofloxacin hydrochloride (AUC: factor 250, $C_{max}$: factor 80). Intratracheal administration of micronized ciprofloxacin-betaine with a particle diameter (50%<3 μm; 90%<7 μm) leads to a further improvement in the pharmacokinetic profile (AUC: factor 612, $C_{max}$: factor 125, compared with intravenous administration of ciprofloxacin hydrochloride).

Efficacy in a Model of Lung Infection with *P. aeruginosa*

Female Wistar rats (80 to 100 g) were infected intratracheally with *P. aeruginosa* DSM 12055 and treated 1 and 4 hours after the infection with ciprofloxacin betaine (laboratory product) intratracheally (i.t.) and with ciprofloxacin hydrochloride intratracheally and intravenously (i.v.). Various dose groups each of 5 rats were employed. The animals were sacrificed 24 hours after the infection, and the lungs were removed and homogenized with a Potter from Braun. The homogenates were plated out to determine the microbe count in the lungs.

The following table shows the reduction in the microbe count in the lungs (log units) after 24 h relative to the untreated infection control (in each case averages for 5 animals):

| Dose group | Reduction in microbe count (log units) |
|---|---|
| A - 0.8 mg/kg ciprofloxacin betaine i.t. | −4.0 |
| B - 2.5 mg/kg ciprofloxacin betaine i.t. | −5.8 |
| C - 7.5 mg/kg ciprofloxacin betaine i.t. | −10 |
| D - 0.8 mg/kg ciprofloxacin hydrochloride i.t. | −1.8 |
| E - 2.5 mg/kg ciprofloxacin hydrochloride i.t. | −1.1 |
| F - 7.5 mg/kg ciprofloxacin hydrochloride i.t. | −2.8 |
| G - 2.5 mg/kg ciprofloxacin hydrochloride i.v. | −2.8 |
| H - 7.5 mg/kg ciprofloxacin hydrochloride i.v. | −3.5 |
| I - 22.5 mg/kg ciprofloxacin hydrochloride i.v. | −5.4 |
| J - 67.5 mg/kg ciprofloxacin hydrochloride i.v. | −8.8 |

Intratracheal use of ciprofloxacin betaine leads to a reduction of from 4 to 10 log units in the microbe count in the lungs in all three dose groups, whereas equal dosages of ciprofloxacin hydrochloride administered intratracheally bring about a far smaller reduction in the microbe count (1.1 to 2.8 log units). Although intravenous administration of ciprofloxacin hydrochloride, the current state of the art, also leads to a marked reduction in the microbe count in the lungs (2.8 to 8.8 log units), this is only with dosages which are 10 times higher. The treatment according to the invention thus leads to a greatly reduced systemic exposure.

In a further test with *P. aeruginosa* DSM 12055, a single intratracheal treatment (1 hour after the infection) was carried out with micronized ciprofloxacin betaine as dry powder. A dose of 10 mg/kg was administered with the aid of a DP-3 dry powder insufflator (PENN-CENTURY, INC.). It is known from control investigations that about 5 to 20% of the administered dose reach the lungs. In this experiment, the microbe count in the lungs was reduced by more than 6 log units compared with an untreated control group.

The invention claimed is:

1. A method of treating a bacterial disease of the lungs in a human or animal comprising the step of locally administering an antibacterially effective amount of a ciprofloxacin embonate or enrofloxacin embonate, in a powder form or powder-containing suspension.

2. A method of treating a bacterial disease of the lungs in a human or animal comprising the step of locally administering an antibacterially effective amount of a ciprofloxacin hemiembonate or enrofloxacin hemiembonate, in a powder form or powder-containing suspension.

3. A method of treating a bacterial disease of the lungs in a human or animal comprising the step of locally administering an antibacterially effective amount of:
    a mixture of ciprofloxacin embonate and ciprofloxacin hemiembonate, or
    a mixture of enrofloxacin embonate and enrofloxacin hemiembonate,
    in a powder form or powder-containing suspension.

* * * * *